United States Patent
Schüth et al.

(10) Patent No.: US 9,206,098 B2
(45) Date of Patent: Dec. 8, 2015

(54) METHOD FOR OBTAINING SUGAR ALCOHOLS HAVING FIVE TO SIX CARBON ATOMS

(71) Applicant: STUDIENGESELLSCHAFT KOHLE MBH, Mülheim an der Ruhr (DE)

(72) Inventors: Ferdi Schüth, Mülheim an der Ruhr (DE); Roberto Rinaldi, Mülheim an der Ruhr (DE); Niklas Meine, Düsseldorf (DE); Jakob Hilgert, Mülheim an der Ruhr (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 14/434,416

(22) PCT Filed: Oct. 4, 2013

(86) PCT No.: PCT/DE2013/100350
§ 371 (c)(1),
(2) Date: Apr. 9, 2015

(87) PCT Pub. No.: WO2014/056486
PCT Pub. Date: Apr. 17, 2014

(65) Prior Publication Data
US 2015/0274618 A1  Oct. 1, 2015

(30) Foreign Application Priority Data
Oct. 9, 2012 (DE) .......................... 10 2012 109 595

(51) Int. Cl.
C07C 29/141 (2006.01)
C07C 31/26 (2006.01)
(52) U.S. Cl.
CPC ............... *C07C 29/141* (2013.01); *C07C 31/26* (2013.01)
(58) Field of Classification Search
CPC .............................. C07C 31/26; C07C 29/141
USPC ......................................... 568/863, 861, 862
See application file for complete search history.

(56) References Cited

U.S. PATENT DOCUMENTS

| 8,062,428 B2 | 11/2011 | Blair et al. |
| 8,945,309 B2 | 2/2015 | Fukuoka et al. |
| 2009/0118494 A1 | 5/2009 | Blair et al. |
| 2009/0217922 A1 | 9/2009 | Fukuoka et al. |
| 2012/0172588 A1 | 7/2012 | Qiao et al. |
| 2013/0239955 A1 | 9/2013 | Schüth et al. |

FOREIGN PATENT DOCUMENTS

| DE | 10 2010 052 602 A1 | 5/2012 |
| EP | 2 011 569 A1 | 1/2009 |
| JP | 2012 041336 A | 3/2012 |
| WO | 2009 061750 A1 | 5/2009 |
| WO | 2011 050424 A1 | 5/2011 |
| WO | 2012 097781 A1 | 7/2012 |

OTHER PUBLICATIONS

Geboers et al; "Efficient hydrolytic hydrogenation of cellulose in the presence of Ru-loaded zeolites and trace amounts of mineral acid"; Chem. Commun., 2011, 47, pp. 5590-5592.
Kobayashi et al; "Synthesis of sugar alcohols by hydrolytic hydrogenation of cellulose over supported metal catalysts"; Green Chem., 2011, 13, p. 326-333.
Han et al; "Direct conversion of cellulose into sorbitol using dual-functionalized catalysts in neutral aqueous solution"; Catalysis Communications 19 (2012) pp. 115-118.
Geboers et al; "Efficient catalytic conversion of concentrated cellulose feeds to hexitols with heteropoly acids and Ru on carbon"; Chem Commun., 2010, 46, pp. 3577-3579.
Luo et al; "Cellulose conversion into polyols catalyzed by reversibly formed acids and supported ruthenium clusters in hot water"; Angew Chem. Int. Ed. 2007, 46, pp. 7636-7639.
International Search Report of corresponding application PCT/DE2013/100350 dated Feb. 24, 2014.

*Primary Examiner* — Elvis O Price
(74) *Attorney, Agent, or Firm* — Norris McLaughlin & Marcus, P.A.

(57) ABSTRACT

The present invention relates to a method for obtaining a high yield of sugar alcohols containing five to six carbon atoms from cellulose-containing materials. In a first step the starting materials (for example microcrystalline cellulose, alpha-cellulose, wood and cellulose-containing residues, such as sugar cane bagasse or wood shavings) and an acid are brought into close contact with the substrates by a impregnation carried out in the liquid or gaseous phase. In addition, in a second step the starting materials impregnated with acid and preferably dried are brought into contact by the action of mechanical energy, such that the cellulose-containing materials are degraded into water-soluble products. Subsequently, in a third step, sugar alcohols having five to six carbon atoms are obtained in a high yield and in high selectivity from the water-soluble products in aqueous solution by hydrolytic hydrogenation by means of a metal-containing catalyst under hydrogen pressure.

14 Claims, 2 Drawing Sheets

METHOD FOR OBTAINING SUGAR ALCOHOLS HAVING FIVE TO SIX CARBON ATOMS

This application is a 371 of International Patent Application No. PCT/DE2013/100350, filed Oct. 4, 2013, which claims foreign priority benefit under 35 U.S.C. §119 of German Patent Application No. 10 2012 109 595.7, filed Oct. 9, 2012, the disclosures of which patent applications are incorporated herein by reference.

The present invention relates to a method for obtaining a high yield of sugar alcohols having five to six carbon atoms from cellulose-containing materials. In a first step the cellulose-containing starting materials (for example microcrystalline cellulose, alpha-cellulose, wood and cellulose-containing residues, such as sugar cane bagasse or wood shavings) and an acid are brought into close contact with the substrates by a saturation or impregnation carried out in the liquid or gaseous phase. In addition, in a second step the starting materials covered with acid and preferably dried are brought into contact by the action of mechanical energy, such that the cellulose-containing materials are degraded into water-soluble products. Subsequently, in a third step, sugar alcohols containing five to six carbon atoms are obtained in a high yield and in high selectivity from the water-soluble products in aqueous solution by hydrolytic hydrogenation by means of a metal-containing catalyst under hydrogen pressure.

The use of biomass as base material for fuels and for chemical basic substances is currently the subject of comprehensive testing. Cellulose, which is the main component of lignocellulose-containing biomass, is considered to be a possible raw material. In order to obtain suitable and workable products, the cellulose must be broken down into smaller molecules.

Already at the start of the 20$^{th}$ century it was attempted to convert cellulose into smaller molecules by non-catalytically-assisted mechanical grinding. Grohn et al. (Journal of Polymer Science 1958, 30, 551) developed a method for converting cellulose into water-soluble products with a conversion rate of 90%, in which the cellulose was ground for 900 hours in a steel vessel.

In the prior art ball mills are usually used to reduce the crystallinity of cellulose. One of the first examples is the use of ball mills to improve the enzymatic hydrolysis of pure and complex cellulose materials (M. Mandels, L. Hontz, J. Nystrom, Biotechnol. Bioeng. 1974, 16, 1471

A further attempt to hydrolyse cellulose catalytically is disclosed in WO 2009/061750, in which a method for producing soluble sugars from a cellulose-containing material is disclosed. The cellulose-containing material is brought into contact with a solid acid and these are ground together over a relatively long period of time so as to obtain a product formed from soluble sugars. However, the used solid acid has the disadvantage that it is virtually consumed during the method, with the result that the catalytic activity decreases during the course of the method and also complete recovery of the catalyst is not possible. To this end, the conversion of the cellulose-containing materials in water-soluble substances is incomplete.

An improved method for obtaining water-soluble sugar oligomers is known from DE10 2010 052 602-A1 without subjecting the products to further processing steps.

The object forming the basis of the present invention was that of providing a method with which a high yield of sugar alcohols containing five to six carbon atoms can be produced easily and efficiently from cellulose-containing material.

The use of catalysts containing transition metals for such methods in order to degrade cellulose is known in principle from EP2011569 and WO 2011050424. These methods suffer from complex method steps and low yields for a number of reasons.

Under consideration of the finding that a pre-treatment may be necessary for the efficient conversion of cellulose into water-soluble oligomers, the inventors have found that the saturation, also referred to as impregnation in accordance with the invention, of the cellulose-containing starting materials, said saturation or impregnation being carried out in a liquid or gaseous phase with a catalytic quantity of a strong acid (for example HCl, $H_2SO_4$ and others), is a very important step for obtaining completely water-soluble oligomers with molecular weights below 2000 Dalton by the action of mechanical forces on the starting materials, which are impregnated with acid and are preferably dried, which oligomers can then be subjected directly, preferably without further preparation, to a hydrogenation treatment in aqueous solution by means of a transition-metal-containing catalyst, and thus for producing a high yield of sugar alcohols containing five to six carbon atoms.

The present invention accordingly relates to a method for obtaining sugar alcohols having five to six carbon atoms from cellulose-containing material or mixtures thereof, in which the cellulose-containing material is brought into close contact with an acid by an impregnation carried out in liquid or gaseous phase, the cellulose-containing material impregnated with the acid and preferably dried is subjected to a mechanical treatment to reduce the degree of polymerisation of the cellulose-containing material, wherein the mechanical treatment is carried out at least until the degradation or cleavage products of the cellulose-containing material are water-soluble in a proportion of more than 60% by weight, preferably more than 70% by weight, particularly more than 80% by weight, even more particularly more than 90% by weight, in relation to the used cellulose-containing material, the obtained reaction product is subjected to a hydrogenation treatment with hydrogen in the presence of a catalyst with a content of transition metal, selected from the metals of groups 3 to 10 of the periodic system (IUPAC) or mixtures thereof, preferably in aqueous solution at a temperature of more than 80° C. and an increased hydrogen pressure. When reference is made in accordance with the invention to cellulose-containing material, mixtures of a number of cellulose-containing materials, which may also be different from one another, are thus also included.

Surprisingly, it has been found that, as a result of the catalytic hydrogenation of the cellulose-containing materials degraded by the action of mechanical forces so as to form water-soluble products, a high yield of sugar alcohols having five to six carbon atoms can be produced if the preferably dried and solid cellulose or the cellulose-containing material is mechanically treated in the presence of a preferably strong acid, for example an inorganic and/or organic acid or mixtures thereof, and that the water-soluble reaction products thus obtained can be subjected, preferably without purification, to a hydrolytic hydrogenation in aqueous solution with hydrogen in the presence of a transition metal catalyst. Sugar alcohols containing five to six carbon atoms, such as hexitols and xylitol, are obtained without significant formation of further by-products.

Here, the cellulose-containing material is not limited to celluloses that have already been purified or to certain celluloses; even untreated natural products such as hay and spruce wood with yields of at least 75% and 87% respectively following 2 hours of grinding, and beech wood or sugar cane bagasse even with yields above 99% after 2 hours of grinding can be converted into water-soluble products, which can then be subjected to the hydrolytic hydrogenation treatment.

Insofar as the term cellulose is used in the present application, this means pure cellulose or cellulose-containing materials. Both natural products, such as wood and grasses, and also chemically pure celluloses and cellulose-containing materials can be used.

When carrying out the method according to the invention an acid is used, selected from inorganic acids, organic acids or mixtures thereof. Here, the acid is used in the method according to the invention in catalytic quantities. The acid is preferably used in a quantity from 0.0001 to 1 mmol per g cellulose.

The impregnation of the cellulose-containing substrates with a strong acid is performed in a diluted acid solution (0.0001 to 6 mol/l) of the acid in a solvent with a low boiling point (for example dimethyl ether, diethyl ether, methylethyl ether, tert-butylmethyl ether, acetone, pentane, hexane, heptane, supercritical carbon dioxide, ethyl acetate, methyl acetate, methanol, dichloromethane, and others) or mixtures thereof, which can be easily removed in a next method step, for example by applying a negative pressure or by feeding heat.

In order to be able to bypass a method step for removing the solvent, the substrate alternatively can be treated with a gaseous acid. In this case cellulose or the cellulose-containing material can be exposed to gaseous HCl, $SO_3$ or other gaseous acids. If desired, however, a combination of the saturation with the impregnation can also be implemented in a gaseous manner, even with different acids.

Particularly good conversion results can be obtained when the inorganic acid has a pKs value <3, preferably a pKs value between −14 and 2. Suitable examples for inorganic acids are mineral acids, such as sulphuric acid, sulphur dioxide, sulphur trioxide, hydrochloric acid, phosphoric acid, phosphotungstic acid and nitric acid, wherein nitric acid is less preferred.

Particularly good conversion results are also obtained when the organic acid has a pKs value <3, preferably a pKs value between −14 and 2. Suitable examples for organic acids are benzenesulfonic acid and derivatives thereof, halogenoalkane carboxylic acid, such as trifluoroacetic acid, or methanesulfonic acid, trifluoroacetic acid and oxalic acid and derivatives thereof.

Mixtures of the above-mentioned acids can also be used. Acids with a pKs value less than −2 are preferred.

In order to carry out the method according to the invention it has proven to be significant that the acid is not brought into contact directly with the cellulose, but that the cellulose-containing material is impregnated in a first method step with a solution of the acid in a suitable solvent and/or with a gaseous acid. Should the impregnation take place in a solution, such solvents, which do not negatively influence the reaction, are suitable, such as water and organic solvents such as diethyl ether, dichloromethane, ethanol, methanol, THF, acetone; benzene, lighter hydrocarbons (for example hydrocarbons containing four to seven carbon atoms) and any other polar or non-polar solvent in which the used acid is soluble or which enables good mixing of cellulose and acid in a dispersion and which has a boiling point of 100° C. or below. In this possible method step the dissolution or dispersion of the acid is mixed with the cellulose-containing material and is left to stand, where appropriate, for a period of time of up to a few hours, particularly up to 2 hours.

Prior to the mechanical treatment of the cellulose, the solvent is removed again, for example by filtration and/or evaporation. In particular when a solvent with a low boiling point, which at normal pressure is from 30 to 80° C., is used as solvent, this can be removed again easily, either by simply heating and/or by applying a negative pressure. The acid, which usually has a higher boiling point, remains on the cellulose material. The mechanical treatment of the cellulose in the presence of the acid may then follow. It has been found that the degree of conversion of the cellulose can be significantly increased by the impregnation of the cellulose material with inorganic and/or organic acid in the presence of a solvent.

Following the removal of the solvent the cellulose-containing material, which is impregnated with acid and is preferably dried, will have a residual moisture of less than 20% by weight, particularly less than 16% by weight, in relation to the total weight of the impregnated cellulose-containing material. During the further course of the method a cellulose-containing material is preferably used that has a residual moisture in the range from 2 to 10% by weight, in relation to the total weight of the impregnated cellulose-containing material, which, if necessary, can be achieved by drying.

The cellulose-containing substrate impregnated with acid and dried can be mechanically treated for example by grinding, extrusion or kneading. Mills can be used that comminute the material to be ground with use of grinding media, such mills for example being vibration mills, agitator mills, agitator bead mills, ball mills, etc. Ball mills are particularly preferred. All extruders known from the prior art can be used as extruder. If the method according to the invention is carried out in a ball mill, for example in a planetary ball mill, rotation rates from 400 to 1,200, preferably 800 to 1,000 rpm, have proven to be suitable. The rotation rate can also be lower in commercial-scale facilities, however a person skilled in the art will be able to fix the rotation rate depending on the used material and the used mill, such that an optimised result can be attained. The reaction time, i.e. the time in which the mechanical treatment occurs, is usually from 0.01 to 24 hours, wherein periods from 1.5 to 12, particularly 2 to 6 hours, are sufficient to obtain a mixture of products with a molecular weight below 2000 Da or completely water-soluble products.

The mechanical treatment is carried out in accordance with the invention at least until the degradation or cleavage products of the cellulose-containing material are water-soluble in a proportion of more than 60% by weight, preferably more than 70% by weight, particularly more than 80% by weight, even more particularly more than 90% by weight, in relation to the used cellulose-containing material. This is generally the case when the degree of polymerisation of the cellulose fragments is less than 15 anhydroglucose units. Depending on the used apparatus for mechanical treatment and the quantity of the used cellulose-containing material, this is generally achieved with a treatment period from 2 to 6 hours, wherein this method duration can be determined by a person skilled in the art in the knowledge of the used facility and the used cellulose-containing materials.

As mentioned above, practically quantitative conversions of the cellulose materials to water-soluble products can be achieved with the method according to the invention. Water-soluble cellulose oligomers, cellobiose and further products are obtained, wherein the formation of by-products (for example 5-hydroxymethylfurfural, furfural, levulinic acid, etc.) can be largely avoided.

The obtained products, also referred to here within the scope of the invention as cellulose cleavage products, which are present in powder form, in particular following grinding in a ball mill, are dissolved in water, where appropriate with separation of non-water-soluble residues, and are subjected to a hydrogenation treatment with hydrogen in the presence of a transition metal catalyst, which generally contains a quantity of up to 10% by weight transition metal in relation to the total weight of the used transition metal.

To this end, the hydrogenation treatment can be carried out in an autoclave with heating of an aqueous solution of the obtained degradation or cleavage products of the cellulose-containing material to a temperature of more than 80° C., particularly between 100° and 200° C., in particular from 120° to 160° C., in the presence of the catalyst at a hydrogen pressure from 10 to 100 bar, particularly 30 to 70 bar, in particular 40 to 60 bar, at a temperature of more than 140° C., particularly between 150° and 200° C., over a period from 0.25 to 24 hours, particularly from 0.5 to 12 hours, in particular from 1 to 6 hours.

Heating of an aqueous solution of the obtained degradation or cleavage products of the cellulose-containing material can also be carried out at a temperature of more than 80° C., particularly between 100° and 200° C., in particular from 120° to 160° C., particularly between 130° and 150° C., over a period from 0.5 to 24 hours, particularly from 0.25 to 12 hours, in particular from 2 to 6 hours, any solid residues produced can be separated off by filtration, and the catalyst can then be added to the filtrate of the heated aqueous solution, and the hydrogenation treatment can be carried out in an autoclave at a hydrogen pressure from 10 to 100 bar, particularly 30 to 70 bar, in particular 40 to 60 bar, at a temperature of more than 140° C., particularly between 150° and 200° C., over a period from 0.25 to 24 hours, particularly from 0.5 to 12 hours, in particular from 1 to 6 hours.

Although in the method according to the invention transition-metal-containing catalysts, which transition metal may be a single metal element or alloys of metal elements, of which the normal potential is in each case positive compared with the hydrogen electrode, such that the metal elements or alloys thereof are not attacked by diluted acids, and may be selected from groups 3 to 11 of the periodic system, such as Pt, Ni, Cu, Ru, Rh, can be used for hydrogenation, the use of a catalyst with a content of metal selected from the elements of the $8^{th}$ to $11^{th}$ group (IUPAC) of the $4^{th}$ to $6^{th}$ period, such as nickel, copper, ruthenium, rhodium, palladium, osmium, iridium, platinum and rhenium, on a substrate that is not attacked by diluted acids, is preferred. Metal oxides or mixed oxides of Si, W, V, Al, Ti, Ce, Zr, Sc, Y, Zr, Ta, Nb, Cr, Mo and/or lanthanides or carbon-containing catalyst substrates (for example activated carbons) are advantageous. By way of example, metal oxides or mixed oxides of Si, W, V, Al, Ti, Ce, Zr, Sc, Y, Zr, Ta, Nb, Cr, Mo and/or lanthanides, or carbon-containing catalyst substrates (for example activated carbons), such as $SiO_2$, $Al_2O_3$, $TiO_2$, $ZrO_2$, $Nb_2O_5$, $W_2O_5$, $WO_3$, $W_2O_3$, $WO_2$, $CeO_2$ and mixed oxides thereof or activated carbon are specified as substrates. The hydrogenation catalyst of the invention particularly comprises ruthenium, which is present in reduced, highly disperse form on a porous carbon substrate. The catalyst comprises at least 0.1% by weight Ru, in relation to the total weight of the catalyst, in order to ensure an at least sufficient catalyst activity. The metal loads on the carbon substrate are preferably 0.5 to 10.0% by weight, particularly 3 to 7% by weight ruthenium, in relation to the total weight of the catalyst.

The recycling experiments with Ru on activated carbon catalyst demonstrated that Ru/C is very stable, even if $H_2SO_4$ is used in the reaction solution. Once the catalyst had been used 6 times, an EDX analysis of the catalyst material revealed that there had been no change in the nominal content of Ru dispersed on carbon-containing substrate. A TEM analysis showed that the Ru nanoparticles on the substrate are enlarged by a treatment of the catalyst for 1 hour at 100 bar hydrogen pressure at 160° C. However, the high selectivity and activity of the catalyst remained practically unchanged. Accordingly, sugar alcohols containing five to six carbon atoms can be obtained in high yields.

It has been found that the metal catalyst such as the Ru/C catalyst for the method according to the invention is preferably subjected to an activation treatment at temperatures of more than 140° C., particularly more than 160° C., and up to 250° C., at a hydrogen pressure of at least 40 bar, particularly at least 50 bar, over a period of time from 0.25 to 2 hours in an autoclave in order to pre-hydrogenate the catalyst and thus enable an improved activity for the hydrolytic hydrogenation of the cellulose cleavage products already at the start of the hydrogenation of the cleavage products. However, it is also possible to use the catalyst in non-activated form and for the reactivity to be increased with the hydrogenation in the method according to the invention. The hydrolytic hydrogenation is thus carried out in accordance with the invention particularly at a pressure from 10 to 100 bar, even more preferably 30 to 70 bar, in particular 40 to 60 bar and at a temperature of more than 140° C., particularly between 150° and 200° C.

The reaction time in which the hydrolytic hydrogenation in accordance with the method according to the invention is carried out is usually from 0.25 to 24 hours, wherein periods from 0.5 to 12 hours, particularly 1 to 6 hours, are usually sufficient.

Following the end of the hydrogenation, the catalyst can be filtered off and used again without resulting in a reduction of activity due to clogging of the catalyst pores with cellulose degradation products, as is observed in methods for hydrogenation of cellulose according to the prior art.

Also under consideration of the fact that the products produced by the mechanocatalytic method are completely water-soluble, this advantage allows the processing of the product mixture to be carried out in a continuous reactor by means of a solid catalyst, which is of great advantage in terms of the process technology. Of course, the method according to the invention can also be carried out batchwise.

The present invention will be explained in greater detail in the following examples, without limiting the invention to these examples.

EXAMPLES

Example 1

Microcrystalline cellulose (Aldrich, 500 mg) was added to water (10 ml). Ruthenium on carbon (100 mg, 5% by weight ruthenium) was added as catalyst. The mixture was heated in an autoclave at a room temperature hydrogen pressure of 50 bar to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 8%. The filtrate was analysed by HPLC in order to determine the product yield. The yield for C6 sugar alcohols (sorbitol, mannitol, sorbitan) was 0%, the yield for xylitol was 0%, other identified compounds together gave a yield of 0.8%.

Example 2

Microcrystalline cellulose (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

A sample of the obtained powder was derivatised with phenyl isocyanate for GPC analysis.

The powder thus obtained (500 mg) was added to water (10 ml). Ruthenium on carbon (100 mg, 5% by weight ruthenium) was added as catalyst. The mixture was heated in an autoclave at a room temperature hydrogen pressure of 50 bar to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 19%.

The filtrate was analysed by HPLC in order to determine the product yield. The yield for C6 sugar alcohols (sorbitol, mannitol, sorbitan) was 0.1%, the yield for xylitol was 0.2%, other identified compounds together gave a yield of 0.8%.

Example 3

Microcrystalline cellulose (500 mg) was added to a 0.05 M sulphuric acid solution (10 ml). Ruthenium on carbon (100 mg, 5% by weight ruthenium) was added as catalyst. The mixture was heated in an autoclave at a room temperature hydrogen pressure of 50 bar to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 13%.

The filtrate was analysed by HPLC in order to determine the product yield. The yield for C6 sugar alcohols (sorbitol, mannitol, sorbitan) was 5.6%, the yield for xylitol was 0.9%, other identified compounds together gave a yield of 0.7%

Example 4

Microcrystalline cellulose (1.20 mg) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was added to 0.05 M sulphuric acid (10 ml). Ruthenium on carbon (100 mg, 5% by weight ruthenium) was added as catalyst. The mixture was heated in an autoclave at a room temperature hydrogen pressure of 50 bar to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 55%.

The filtrate was analysed by HPLC in order to determine the product yield. The yield for C6 sugar alcohols (sorbitol, mannitol, sorbitan) was 44.7%, the yield for xylitol was 3.0%, other identified compounds together gave a yield of 0.5%.

Example 5

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure. A sample of the powder thus obtained was derivatised with phenyl isocyanate for GPC analysis.

The powder thus obtained (500 mg) was added to water (10 ml). Ruthenium on carbon (100 mg, 5% by weight ruthenium) was added as catalyst. The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 32%.

The filtrate was analysed by HPLC in order to determine the product yield. The yield for C6 sugar alcohols (sorbitol, mannitol, sorbitan) was 9.0%, the yield for xylitol was 1.3%, other identified compounds together gave a yield of 0.8%.

Example 6

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 1 hour. The rotational frequency of the main disc was 800 rpm.

A sample of the powder obtained was derivatised with phenyl isocyanate for GPC analysis.

The powder thus obtained (500 mg) was added to water (10 ml). Ruthenium on carbon (100 mg, 5% by weight ruthenium) was added as catalyst. The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 96%.

The filtrate was analysed by HPLC in order to determine the product yield. The yield for C6 sugar alcohols (sorbitol, mannitol, sorbitan) was 71.8%, the yield for xylitol was 5.5%, other identified compounds together gave a yield of 6.5%.

Example 7

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

A sample of the powder obtained was derivatised with phenyl isocyanate for GPC analysis. The powder thus obtained was completely water-soluble.

The powder thus obtained (500 mg) was dissolved in water (10 ml). Ruthenium on carbon (100 mg, 5% by weight ruthenium) was added as catalyst. The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 100%.

The filtrate was analysed by HPLC in order to determine the product yield. The yield for C6 sugar alcohols (sorbitol, mannitol, sorbitan) was 87.6%, the yield for xylitol was 5.3%, other identified compounds together gave a yield of 4.3%.

Example 8

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 3 hours. The rotational frequency of the main disc was 800 rpm.

A sample of the powder obtained was derivatised with phenyl isocyanate for GPC analysis. The powder thus obtained was completely water-soluble.

The powder thus obtained (500 mg) was dissolved in water (10 ml). Ruthenium on carbon (100 mg, 5% by weight ruthenium) was added as catalyst. The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 100%.

The filtrate was analysed by HPLC in order to determine the product yield. The yield for C6 sugar alcohols (sorbitol, mannitol, sorbitan) was 79.6%, the yield for xylitol was 6.0%, other identified compounds together gave a yield of 3.6%.

Example 9

α-cellulose (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

A sample of the powder obtained was derivatised with phenyl isocyanate for GPC analysis.

The powder thus obtained (500 mg) was dissolved in 0.05 M sulphuric acid (10 ml).

Ruthenium on carbon (100 mg, 5% by weight ruthenium) was added as catalyst. The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 62%.

The filtrate was analysed by HPLC in order to determine the product yield. The yield for C6 sugar alcohols (sorbitol, mannitol, sorbitan) was 32%, the yield for xylitol was 12.6%, other identified compounds together gave a yield of 1.6%.

Example 10

α-cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure. A sample of the powder thus obtained was derivatised with phenyl isocyanate for GPC analysis.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

A sample of the powder obtained was derivatised with phenyl isocyanate for GPC analysis.

The powder thus obtained (500 mg) was dissolved in water (10 ml). Ruthenium on carbon (100 mg, 5% by weight ruthenium) was added as catalyst. The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filter cake was washed, dried and weighed. The conversion was calculated by the weight difference of cellulose. The conversion was 100%.

The filtrate was analysed by HPLC in order to determine the product yield. The yield for C6 sugar alcohols (sorbitol, mannitol, sorbitan) was 85.9%, the yield for xylitol was 13.7%, other identified compounds together gave a yield of 0.4%.

Example 11

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). Ruthenium on carbon (100 mg, 5% by weight ruthenium) was added as catalyst. The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filter cake was washed with water (60 ml) and acetone (60 ml), dried and used a number of times as catalyst by being added to a freshly presented solution of sulphuric-acid-impregnated ground microcrystalline cellulose (500 mg) in water (10 ml) as described in this example.

The filtrate was analysed by HPLC in order to determine the product yield.

After the first test the yield for C6 sugar alcohols (sorbitol, mannitol) was 81.3%, the yield for xylitol was 5.7%, the yield for sorbitan was 6.0%, other identified compounds together gave a yield of 1.2%.

After the second test the yield for C6 sugar alcohols (sorbitol, mannitol) was 85.1%, the yield for xylitol was 5.7%, the yield for sorbitan was 5.8%, other identified compounds together gave a yield of 1.0%.

After the third test the yield for C6 sugar alcohols (sorbitol, mannitol) was 85.2%, the yield for xylitol was 4.6%, the yield for sorbitan was 5.3%, other identified compounds together gave a yield of 0.8%.

After the fourth test the yield for C6 sugar alcohols (sorbitol, mannitol) was 85.9%, the yield for xylitol was 3.8%, the yield for sorbitan was 4.7%, other identified compounds together gave a yield of 1.0%.

After the fifth test the yield for C6 sugar alcohols (sorbitol, mannitol) was 89.0%, the yield for xylitol was 3.9%, the yield for sorbitan was 4.5%, other identified compounds together gave a yield of 1.0%.

After the sixth test the yield for C6 sugar alcohols (sorbitol, mannitol) was 86.2%, the yield for xylitol was 3.8%, the yield for sorbitan was 4.6%, other identified compounds together gave a yield of 0.8%.

Example 12

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). The catalyst was activated prior to the reaction. To this end, ruthenium on carbon (100 mg, 5% by weight ruthenium) was suspended in water (10 ml). The suspension was heated in an autoclave at a room temperature hydrogen pressure of 50 bar for 1 hour to 160° C. The catalyst was filtered off, washed (60 ml water, 60 ml acetone) and dried before it was added to the solution.

The mixture was heated in an autoclave at a room temperature hydrogen pressure of 50 bar for 1 hour to 140° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 77.7%, the yield for sorbitan was 2.8%, the yield for xylitol was 3.7%, other identified compounds together gave a yield of 6.1%.

Example 13

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). Ruthenium on carbon (100 mg, 5% by weight ruthenium) was added as non-activated catalyst.

The mixture was heated in an autoclave at a room temperature hydrogen pressure of 50 bar for 1 hour to 140° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 54.5%, the yield for sorbitan was 1.6%, the yield for xylitol was 2.2%, other identified compounds together gave a yield of 0.4%.

Example 14

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). The catalyst was activated prior to the reaction. To this end, ruthenium on carbon (100 mg, 5% by weight ruthenium) was suspended in water (10 ml). The suspension was heated in an autoclave at a room temperature hydrogen pressure of 50 bar for 1 hour to 160° C. The catalyst was filtered off, washed (60 ml water, 60 ml acetone) and dried before it was added to the solution.

The mixture was heated in an autoclave at a room temperature hydrogen pressure of 50 bar for 1 hour to 150° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 90.1%, the yield for sorbitan was 4.3%, the yield for xylitol was 4.6%, other identified compounds together gave a yield of 0.9%.

Example 15

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). Ruthenium on carbon (100 mg, 5% by weight ruthenium) was added as non-activated catalyst.

The mixture was heated in an autoclave at a room temperature hydrogen pressure of 50 bar for 1 hour to 150° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 84.6%, the yield for sorbitan was 4.2%, the yield for xylitol was 3.6%, other identified compounds together gave a yield of 0.7%.

Example 16

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). The catalyst was activated prior to the reaction. To this end, ruthenium on carbon (100 mg, 5% by weight ruthenium) was suspended in water (10 ml). The suspension was heated in an autoclave at a room temperature hydrogen pressure of 50 bar for 1 hour to 160° C. The catalyst was filtered off, washed (60 ml water, 60 ml acetone) and dried before it was added to the solution.

The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 83.8%, the yield for sorbitan was 6.6%, the yield for xylitol was 6.4%, other identified compounds together gave a yield of 2.9%.

Example 17

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). Ruthenium on carbon (100 mg, 5% by weight ruthenium) was added as non-activated catalyst.

The mixture was heated in an autoclave at a room temperature hydrogen pressure of 50 bar for 1 hour to 160° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 82.0%, the yield for sorbitan was 5.6%, the yield for xylitol was 5.3%, other identified compounds together gave a yield of 2.1%.

Example 18

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). The catalyst was activated prior to the reaction. To this end, ruthenium on carbon (100 mg, 5% by weight ruthenium) was suspended in water (10 ml). The suspension was heated in an autoclave at a room temperature hydrogen pressure of 50 bar for 1 hour to 200° C. The catalyst was filtered off, washed (60 ml water, 60 ml acetone) and dried before it was added to the solution.

The mixture was heated in an autoclave at a room temperature hydrogen pressure of 50 bar for 1 hour to 130° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 78.9%, the yield for sorbitan was 2.2%, the yield for xylitol was 2.9%, other identified compounds together gave a yield of 1.6%.

Example 19

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). Ruthenium on carbon (100 mg, 5% by weight ruthenium) was added as non-activated catalyst.

The mixture was heated in an autoclave at a room temperature hydrogen pressure of 50 bar for 1 hour to 130° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 46.0%, the yield for sorbitan was 0.0%, the yield for xylitol was 2.3%, other identified compounds together gave a yield of 4.3%.

Example 20

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). The catalyst was activated prior to the reaction. To this end, ruthenium on carbon (100 mg, 5% by weight ruthenium) was suspended in water (10 ml). The suspension was heated in an autoclave at a room temperature hydrogen pressure of 50 bar for 1 hour to 200° C. The catalyst was filtered off, washed (60 ml water, 60 ml acetone) and dried before it was added to the solution.

The mixture was heated in an autoclave at a room temperature hydrogen pressure of 50 bar for 1 hour to 140° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 86.7%, the yield for sorbitan was 6.7%, the yield for xylitol was 6.7%, other identified compounds together gave a yield of 1.8%.

Example 21

Microcrystalline cellulose (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.20 g) was ground in a steel beaker using steel balls (6 steel balls; individual weight 3.95 g) in a Pulverisette P7 mill from the company Fritsch for 2 hours. The rotational frequency of the main disc was 800 rpm.

The powder thus obtained (500 mg) was dissolved in water (10 ml). The catalyst was activated prior to the reaction. To this end, ruthenium on carbon (100 mg, 5% by weight ruthenium) was suspended in water (10 ml). The suspension was heated in an autoclave at a room temperature hydrogen pressure of 50 bar for 1 hour to 200° C. The catalyst was filtered off, washed (60 ml water, 60 ml acetone) and dried before it was added to the solution.

The mixture was heated in an autoclave at a room temperature hydrogen pressure of 50 bar for 1 hour to 150° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for C6 sugar alcohols (sorbitol, mannitol) was 89.2%, the yield for sorbitan was 4.2%, the yield for xylitol was 4.5%, other identified compounds together gave a yield of 1.0%.

Example 22

Beech wood shavings were processed using a blender to form a powder. The powder was sieved and the proportion of particles smaller than 250 μm was reused.

This powder (10 g) was dispersed in tert-butylmethyl ether (150 ml) and sulphuric acid (0.52 mL, 95-97%, commercial product from the company J. T. Baker, USA) was added dropwise. The suspension was stirred for 1 hour before the solvent was removed at reduced pressure.

The powder thus obtained (1.00 g) was ground in a steel beaker using steel balls (6 steel balls; individual weight 3.95 g) in a Pulverisette P7 mill from the company Fritsch for 3 hours. The rotational frequency of the main disc was 800 rpm.

The powder thus obtained (900 mg) was dissolved in water (9 ml) in 8 parallel batches. The solution was heated for 1 hour to 145° C., the solid created during this process was separated off by filtration, and the filtrate of the combined batches was analysed by HPLC.

The solution therefore contained cellobiose (0.88 mg/ml), glucose (35.99 mg/ml), xylose (20.09 mg/ml), C6 sugar alcohols (sorbitol and mannitol: 0.54 mg/ml), glycerol (0.28 mg/ml), levulinic acid (0.30 mg/ml), 5-hydroxymethylfurfural (0.44 mg/ml) and furfural (0.93 mg/ml). The catalyst was activated prior to the reaction. To this end, ruthenium on carbon (100 mg, 5% by weight ruthenium) was suspended in water (10 ml). The suspension was heated in an autoclave at a room temperature hydrogen pressure of 50 bar for 1 hour to 200° C. The catalyst was filtered off, washed (60 ml water, 60 ml acetone) and dried before it was added to the solution.

The mixture was heated in an autoclave at a room temperature hydrogen pressure of 50 bar for 1 hour to 145° C. Upon reaching the reaction temperature, the measurement of the reaction time was started. After 60 min reaction time the autoclave was cooled in an ice-cooled water bath before it was opened.

The reaction mixture was filtered. The filtrate was analysed by HPLC in order to determine the product yield.

The yield for the C6 compounds (sorbitol, mannitol and glucose) was calculated relative to the concentration of glucose and cellobiose in the reaction solution prior to the reaction. The C6 sugar alcohol yield (sorbitol, mannitol) was 84.0%, the glucose yield was 13.4%. The yield for xylitol (84.2%) and xylose (11.7%) were calculated relative to the concentration of xylose in the reaction solution prior to the reaction. Furthermore, glycerol, 1,3-propanediol, methanol, levulinic acid, hydroxymethylfurfural and furfural and furan acid were identified as by-products.

The analysis data mentioned in the above examples is presented in the following table.

TABLE 1

Results of the hydrolytic hydrogenation of non-processed and ball-ground substrates.[a]

| No. | Substrate | Grinding time (h) | Reaction medium | Conversion (%)[b] | Carbon yields (%) | | | | | Mass balance (%) |
|---|---|---|---|---|---|---|---|---|---|---|
| | | | | | C$_6$-Alditols | Sorbitan | Hexitols Sum | Xylitol | Other | |
| 1 | | 0 | H$_2$O | 8 | 0.0 | 0.0 | 0.0 | 0.0 | 0.8 | 10 |
| 2 | Microcrystalline | 2 | H$_2$O | 19 | 0.1 | 0.0 | 0.1 | 0.2 | 0.8 | 6 |

TABLE 1-continued

Results of the hydrolytic hydrogenation of
non-processed and ball-ground substrates.[a]

| | | Grinding | | | Conversion | Carbon yields (%) | | | | Mass |
|---|---|---|---|---|---|---|---|---|---|---|
| No. | Substrate | time (h) | Reaction medium | (%)[b] | $C_6$-Alditols | Sorbitan | Hexitols Sum | Xylitol | Other | balance (%) |
| 3 | cellulose (MCC) | 0 | 0.05M $H_2SO_4$ | 13 | 4.8 | 0.8 | 5.6 | 0.9 | 0.7 | 55 |
| 4 | | 2 | 0.05M $H_2SO_4$ | 55 | 41.6 | 3.1 | 44.7 | 3.0 | 0.5 | 88 |
| 5 | $H_2SO_4$- | 0 | $H_2O$ | 32 | 7.8 | 1.2 | 9.0 | 1.3 | 0.8 | 35 |
| 6 | impregnated | 1 | $H_2O$ | 96 | 66.8 | 5.0 | 71.8 | 5.5 | 6.5 | 87 |
| 7 | MCC (IMMC) | 2 | $H_2O$ | 100[c] | 82.0 | 5.6 | 87.6 | 5.3 | 4.3 | 97 |
| 8 | | 3 | $H_2O$ | 100[c] | 73.9 | 5.7 | 79.6 | 6.0 | 3.6 | 89 |
| 9 | α-cellulose | 2 | 0.05M $H_2SO_4$ | 62 | 32.0 | 0.0 | 32.0 | 12.6 | 1.6 | 75 |
| 10 | $H_2SO_4$-impregnated α-cellulose | 2 | $H_2O$ | 100[c] | 80.3 | 5.6 | 85.9 | 13.7 | 0.4 | 100 |
| 11 | Glucose | 0 | 0.05M $H_2SO_4$ | 100[c] | 92.6 | 3.7 | 96.3 | 2.1 | 1.6 | 100 |

[a]Reaction conditions: 500 mg substrate, 10 mL water, 100 mg Ru/C, 50 bar H2 (r.t.), 16° C., 1 h.
[b]The conversion was determined via the weight difference.
[c]The substrates were soluble in water, the solution had a pH = 1.

The present invention will be explained in further detail by the accompanying figures, in which.

Figure 1:
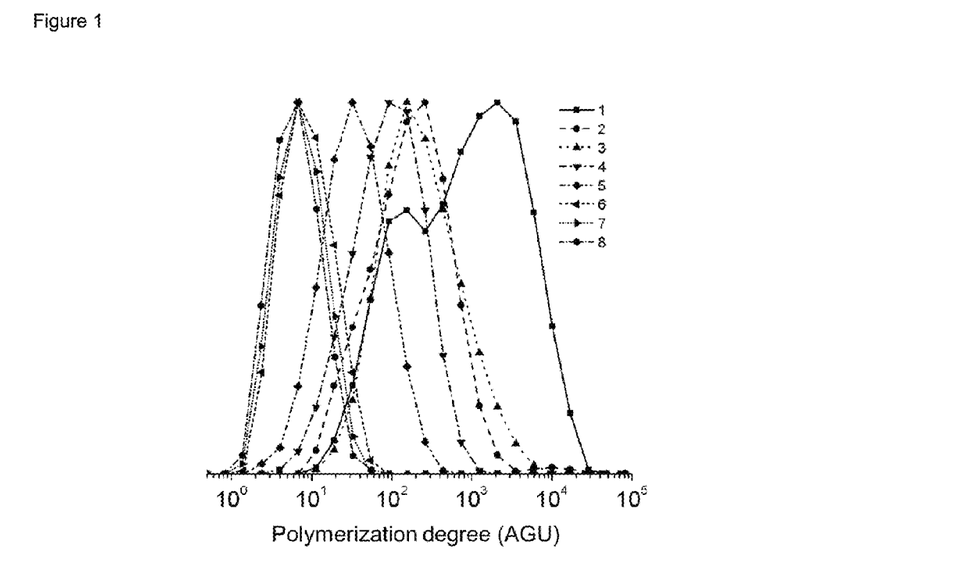
FIG. 1 shows the degree of polymerisation of the phenyl carbanylate derivative of α-cellulose (1), MCC (2), α-cellulose ground in a ball mill for 2 h (3), MCC ground in a ball mill for 2 h (4), IMCC (5), IMCC ground in a ball mill for 1 h (6), 2 h (7) and 3 h (8).
Figure 2:
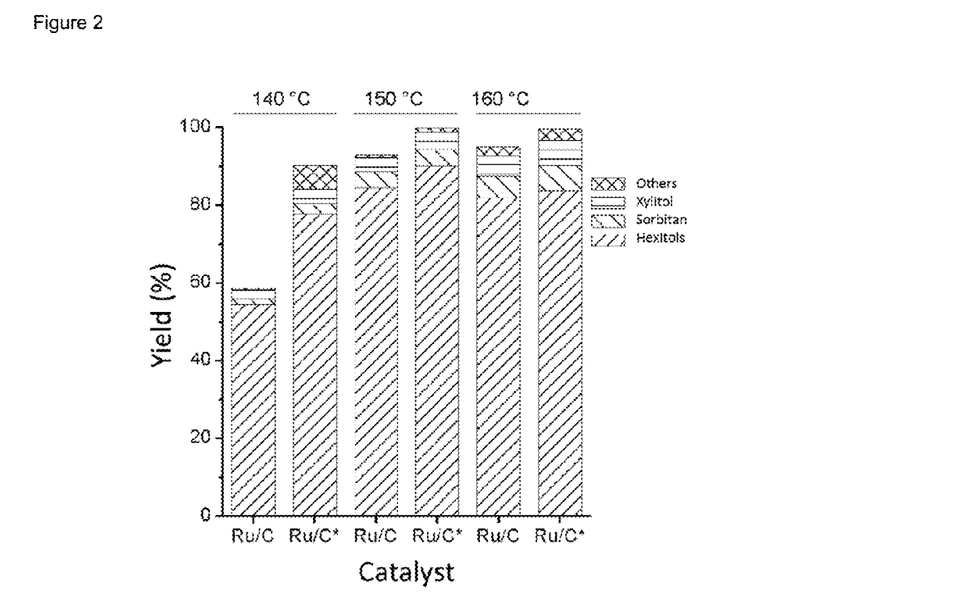
FIG. 2 shows the comparison of the performance of Ru/C and Ru/C* catalysts with the hydrolytic hydrogenation of IMCC ground in a ball mill for 2 h: 500 mg substrate, 10 mL water, 100 mg catalyst, 50 bar $H_2$ (r.t.), 1 h. The reaction temperatures are specified at the top in the figure.
Figure 3:
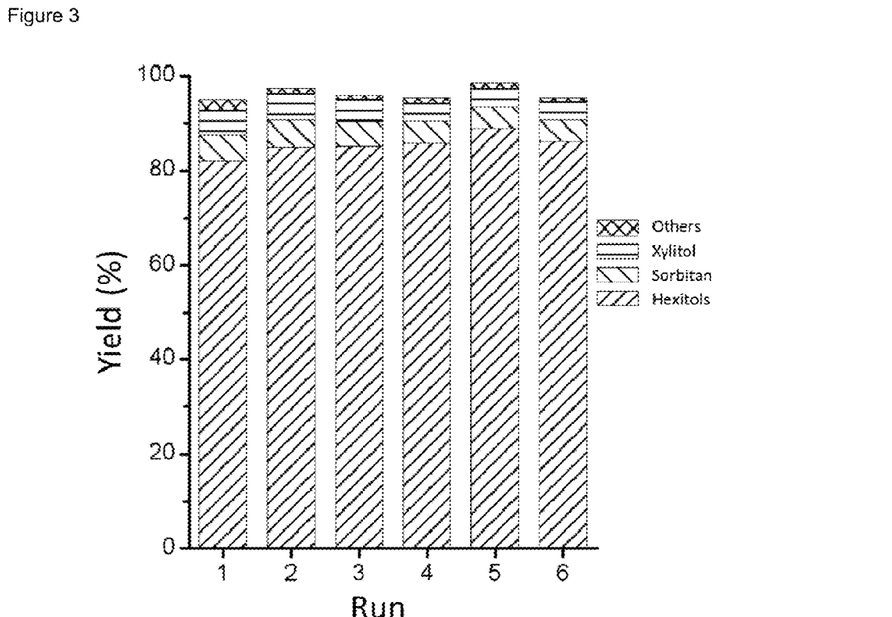
FIG. 3 shows the recycling of Ru/C. Reaction conditions: 500 mg IMCC ground in a ball mill for 2 h, 10 mL water, 100 mg Ru/C, 50 bar $H_2$ (r.t.), at 160° C. for 1 h.
Figure 4:
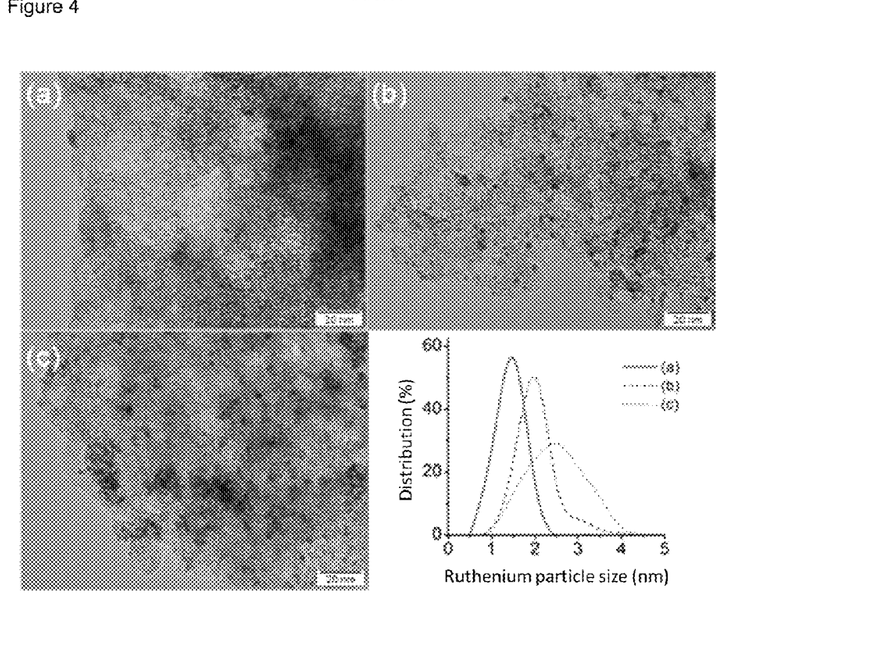
FIG. 4 shows TEM images of the Ru/C catalysts: (a) prior to the reaction, (b) after one cycle and (c) after 6 cycles. The image in the bottom right corner shows the Ru particle distribution of the catalyst samples.

The invention claimed is:

1. A method for obtaining sugar alcohols having five to six carbon atoms from cellulose-containing material or mixtures thereof, said method comprising (a) bringing the cellulose-containing starting material into close contact with an acid by an impregnation carried out in the liquid or gaseous phase, (b) subjecting the cellulose-containing material impregnated with the acid and optionally dried to a mechanical treatment in order to reduce the degree of polymerisation of the cellulose-containing material, wherein the mechanical treatment is carried out at least until the degradation or cleavage products of the cellulose-containing material are water-soluble in a proportion of more than 60% by weight, in relation to the used cellulose-containing material, and (c) subjecting the obtained reaction product to a hydrogenation treatment with hydrogen in the presence of a catalyst with a content of transition metal elements, selected from the group consisting of elements of groups 3 to 10 of the periodic system (IUPAC) and mixtures thereof.

2. The method according to claim 1, wherein the acid has a pKs value from −14 to 2.

3. The method according to claim 1, wherein the impregnation is carried out with a solution of an acid in a liquid phase and the solvent is separated off after an exposure time.

4. The method according to claim 1, wherein the impregnation is carried out with an acid in the gaseous phase.

5. The method according to claim 1, wherein the acid is used in a catalytic quantity.

6. The method according to claim 1, wherein the mechanical treatment is a grinding, wherein the material to be ground is comminuted in a mill with use of grinding media.

7. The method according to claim 6, wherein the mill is at least one selected from the group consisting of a vibration mill, agitator mill, agitator bead mill and ball mill.

8. The method according to claim 1, wherein the material obtained following the mechanical treatment is subjected to a method step for neutralisation of the acid.

9. The method according to claim 1, wherein a hydrogenation catalyst with a content of platinum metal, selected from the elements of the $8^{th}$ to $10^{th}$ group (IUPAC) of the $4^{th}$ to $6^{th}$ period, is used on an inorganic, organic or hybrid substrate, or carbon-containing catalyst substrates.

10. The method according to claim 1, wherein a hydrogenation catalyst ruthenium in reduced form on a porous carbon substrate containing at least 0.1% by weight Ru in relation to the total weight of the catalyst is used.

11. The method according to claim 10, wherein an Ru/C hydrogenation catalyst was subjected to an activation treatment at temperatures of more than 140° C. at a hydrogen pressure of at least 40 bar over a period from 0.5 to 2 hours, in an autoclave.

12. The method according to claim 1, wherein the hydrolytic hydrogenation is carried out at a hydrogen pressure from 10 to 100 bar at a temperature of more than 140° C. over a period from 0.25 to 24 hours.

13. The method according to claim 1, wherein at least the hydrolytic hydrogenation is carried out as a continuous method step.

14. The method according to claim 1, wherein the hydrogenation catalyst is filtered off following hydrogenation and is provided for a further hydrogenation.

* * * * *